(12) United States Patent
Legge et al.

(10) Patent No.: US 7,238,533 B1
(45) Date of Patent: Jul. 3, 2007

(54) PERSONAL ILLICIT DRUG DETECTION METHOD

(76) Inventors: Ronald Legge, 1641 W. Frye Rd., Phoenix, AZ (US) 84045; Theresa Hopson, 2502 Carol, Mesa, AZ (US) 85204; George Maracas, 2613 E. Bighorn, Phoenix, AZ (US) 85048; Pamela Bechtel, 8840 Costa Verde Blvd., San Diego, CA (US) 92122

( * ) Notice: Subject to any disclaimer, the term of this patent is extended or adjusted under 35 U.S.C. 154(b) by 543 days.

(21) Appl. No.: 10/624,703

(22) Filed: Jul. 22, 2003

(51) Int. Cl.
*G01N 33/48* (2006.01)
(52) U.S. Cl. .............. 436/166; 436/164; 436/816; 436/901; 436/165; 422/61; 422/58
(58) Field of Classification Search ............ 422/58, 422/61; 436/164–166, 816, 901
See application file for complete search history.

(56) References Cited

U.S. PATENT DOCUMENTS

| | | | |
|---|---|---|---|
| 5,662,911 A | 9/1997 | Huber et al. | |
| 5,879,896 A | 3/1999 | Hinuma et al. | |
| 6,153,147 A | 11/2000 | Craig | |
| 6,156,431 A | 12/2000 | Kitchen et al. | |
| 6,465,791 B1 * | 10/2002 | Ribi et al. | 250/372 |
| 2002/0006444 A1 * | 1/2002 | Konishi | 424/725 |
| 2003/0175224 A1 * | 9/2003 | Arndt | 424/61 |
| 2004/0071645 A1 * | 4/2004 | Bohn et al. | 424/61 |

* cited by examiner

*Primary Examiner*—Lyle A. Alexander
(74) *Attorney, Agent, or Firm*—Parsons & Goltry; Robert A. Parsons; Michael W. Goltry

(57) ABSTRACT

Personal illicit drug detecting apparatus is disclosed which includes a substance chemically reactive to a suspected drug. The substance is provided in the form of a layer positioned on at least one finger of a user. The substance can be blended into finger nail polish and positioned on at least one nail by painting or positioned anywhere on a finger in the form of a decal. To test a suspected beverage the user inconspicuously moistens the substance on the finger or finger nail with liquid from a beverage and observes any change (e.g. color, image, etc.) of the layer on the finger nail or finger nail, wherein the change indicates the presence of the suspected drug in the beverage.

8 Claims, 1 Drawing Sheet

US 7,238,533 B1

PERSONAL ILLICIT DRUG DETECTION METHOD

FIELD OF THE INVENTION

This invention relates to illicit drug detecting apparatus and methods.

BACKGROUND OF THE INVENTION

At the present time, the manufacture of various drugs and the availability to ordinary people has greatly promoted the illicit use of some of these drugs for unsavory purposes. For example, it is not uncommon to read in the news about women that have gone into a bar, night club, or similar establishment with friends or a date and been drugged and raped. The drugging is generally a result of someone surreptitiously introducing the drug into a woman's drink. The woman, believing she is simply drinking an alcoholic beverage, consumes part or all of the drink and becomes disoriented or unconscious, depending upon the dosage and the amount she drinks. She is then vulnerable to be taken from the premises and physically misused.

A typical drug used for such purposes is flunitrazepam, with a trade name Rohypnol®, and a street name roofies. Flunitrazepam belongs to the benzodiazepine family of medications. It is not marketed in the United States, but it is an approved medication in most other parts of the world, where it is prescribed mainly for short-term treatment of sleep disorders. Flunitrazepam is ten times more potent than Valium®. Continued use results in physical dependency. Flunitrazepam obtained for illicit use in the United States is usually purchased in Mexico and transported across the border. It is used along with alcohol to heighten the feeling of drunkenness.

When taken alone flunitrazepam is not likely to be lethal, but when mixed with alcohol it is more likely to be lethal due to the enhanced sedating effects on the central nervous system. Persons who become intoxicated from mixing flunitrazepam and alcohol may pass out and remain out for 8-24 hours. Flunitrazepam has also been reported to be used in combination with other drugs: to ease the coming down effect of a cocaine or crack high, or to enhance a heroin high. Flunitrazepam is usually swallowed as a pill or dissolved in a drink. Its use is spreading among high school and college youths. Flunitrazepam is becoming known as a club drug and has reportedly been used as a "date rape drug".

Another major date-rape drug used in many instances is gamma hydoxybutyrate, known as GHB. As explained above, the drug is added to a drink and produces similar results.

Many women and young girls are subjected to flunitrazepam, GHB, or similar acting drugs without their knowledge or permission. This is a serious problem. Many women and especially young girls want to be socially active and join in the consumption of alcoholic beverages during parties, dates, etc. However, the danger of being drugged and physically accosted is real and places a heavy burden on the enjoyment. Some tests for the drugs are available but they generally consist of very complicated and lengthy or very obvious procedures. Most women do not want to offend their friends and/or dates by testing their drinks before consumption or prior to each taste of the drink.

It would be highly advantageous, therefore, to remedy the foregoing and other deficiencies inherent in the prior art.

Accordingly, it is an object the present invention to provide a new and improved personal illicit drug detector and method.

A further object of the present invention is to provide a personal illicit drug detector and method that is unobvious, inconspicuous and substantially unnoticeable.

Another object of the present invention is to provide a new and improved personal illicit drug detector and method that provides immediate protection without inciting displeasure or ire in friends and companions.

SUMMARY OF THE INVENTION

The above problems and others are at least partially solved and the above purposes and others realized in a new and improved personal illicit drug detecting apparatus including a layer with a substance chemically reactive to a suspected drug. The layer is positioned on at least one fingernail of a user. The substance can be blended into finger nail polish and positioned on at least one nail by painting or in the form of a decal or it can simply include the substance if the person does not use finger nail polish. The finger nail can then be inconspicuously moistened with liquid from a suspected drink. If the layer turns color the drink contains the suspected drug and should be discarded or otherwise left.

It is further contemplated that a plurality of finger nails can be provided with layers of the substance on each nail. The plurality of nails can then be used a plurality of times to test the same drink at different times or different drinks at different times. In a still further embodiment, substances for different suspected drugs can be positioned on different nails and tests for the different drugs can be performed on the same or different beverages. In each of the above tests the procedure can be performed inconspicuously and without arousing the interest or suspicion of any companions at the table.

BRIEF DESCRIPTION OF THE DRAWINGS

The foregoing and further and more specific objects and advantages of the invention will become readily apparent to those skilled in the art from the following detailed description taken in conjunction with the drawings in which.

DETAILED DESCRIPTION OF A PREFERRED EMBODIMENT

The manufacture and availability of various drugs has greatly promoted the illicit use of some of these drugs for unsavory purposes. For example, it is not uncommon for women that have gone into a bar, night club, or similar establishment with friends or a date to be drugged and raped. The drugging is generally a result of someone surreptitiously introducing the drug into the woman's drink. The woman, believing she is simply drinking an alcoholic beverage, consumes part or all of the drink and becomes disoriented or unconscious, depending upon the dosage and the amount she drinks.

Many different devices or systems have been devised in attempts to solve this problem. In most instances the device cannot be used conveniently without attracting attention and, in many instances, arousing the ire of the woman's companion. For example, drink coasters, test strips, cards, etc. have been devised that have test spots or portions on them (see for example, U.S. Pat. No. 6,153,147). The person with the suspected drink must then somehow splash a small amount of her drink on one of the spots or dip the test strips in the drink and observe the spot to determine if a color change occurs. In most instances the color change does not occur until the spot is dry, which can take a relatively long time. The problem here is that it can be difficult to splash the correct amount of drink onto the coaster or dip a strip of paper in the drink unnoticed. Chiefly this action can attract attention and in many instances make the woman appear sloppy and/or indiscreet.

Another example of a drink testing device is a swizzle stick with a treated disc on one end. The user is encouraged or instructed to place the swizzle stick in her drink just like with a normal swizzle stick. Anytime the drink is left unattended by the woman for a short time, such as by a trip to the bathroom, she is instructed to simply reverse the swizzle stick and dip the treated disc end into the drink. The problem here is that in many instances the drink comes with a swizzle stick and the woman must discard the original and replace it with the treated swizzle stick. This action can be noticeable and highly questionable. Also, to reverse the stick and place it in the drink while observing it for color change can again be very noticeable and highly questionable. These actions are difficult to perform without raising the interest of companions at the table.

Figure 1:
FIG. 1 illustrates a woman in a typical situation with a personal illicit drug detector disposed on one or more fingernails, in accordance with the present invention.
Figure 2:
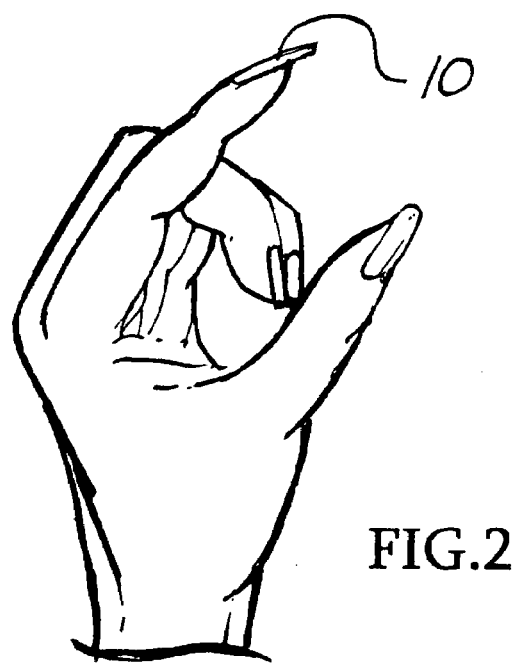
FIG. 2 is an enlarged view of the fingernails from FIG. 1 illustrating in more detail the disposition of the personal illicit drug detector of the present invention.

Turning to the drawings, in which like reference characters indicate corresponding elements throughout the several views, attention is first directed to FIG. 1, which illustrates a woman sitting at a cocktail table with an alcoholic beverage before her. The woman has a personal illicit drug detector 10 disposed on one or more fingernails, in accordance with the present invention. Drug detector 10 includes a layer having a substance chemically reactive to a suspected drug positioned, preferably, on at least one fingernail of the user. The layer can be, for example, a blend of the chemically reactive substance and finger nail polish that is positioned on the finger nail, either by means of a decal or simply painted on the nail. An enlarged view of drug detector 10 on a finger nail is illustrated in FIG. 2. Here it should be understood that drug detectors in the form of decals or appliqués can be conveniently placed in other positions on a finger, such as under the finger nail, on the pad of the finger, etc.

The user can, very discreetly, moisten drug detector 10 on her finger nail with her drink without raising suspicion or otherwise appear to be doing anything different. Drug detector 10 will dry relatively rapidly because of the natural body heat and any color change can be discreetly observed without raising any suspicion or interest in companions at the table. Here it should be noted that the detection apparatus is not limited to a color change, upon detection of a suspected drug, but could include, for example, an image change or the like. Thus, the woman can be safe without raising the interest and/or ire of companions at the table or at the party.

It is anticipated that a woman may want to provide more than one drug detector 10 on more than one finger nail, for the instance where more than one drink is consumed or where some intervening circumstance has occurred between an initial test and the finishing of the drink. Also, it may be desirable to provide several (two or more) drug detectors that include different chemically reactive substances to test for different drugs, although in many instances (e.g. where the drug detector is capable of sensing a large variety of illicit drugs) this may not be necessary.

Chemically reactive substances for the purpose described are well known and will not be described in detail, except to list some examples below. It is known, for example, to use unique mixtures of monoclonal and polyclonal antibodies to selectively identify methadone, opiates, marijuana, amphetamine, cocaine, benzodiazepine and their metabolites. A composition made by treating a particular silica with phenyltrichlorosilane and with 3-mercaptopropyltrimethoxysilane useful in detecting the presence of GHB in a liquid is described in U.S. Pat. No. 6,156,431.

It should be understood that the described testing apparatus is capable of testing for the presence of many drugs other than those mentioned above and the specific drugs mentioned are only for purposes of example and are not intended to limit the scope of the invention. Also, while the drug detector 10 is described as including a "layer" of a chemically reactive substance, it should be understood that the layer could include a capillary coating wherein the chemically reactive substance is contained within the capillaries and the reaction takes place within the capillaries. For example, a decal could be constructed as a capillary-filled structure and applied as a layer. Alternatively, the layer could consist of appropriately sized pores containing the chemically reactive substance or, for example, a heavy metal that acts as a reaction site and is trapped in the pores. In this example, the size of the pores is chosen such that the heavy metals are trapped and don't leach out into the environment.

Thus, a new and improved personal illicit drug detector and method have been disclosed. Use of the personal illicit drug detector and method is unobvious, inconspicuous and substantially unnoticeable so that drinks can be discreetly tested to provide immediate protection without inciting displeasure or ire in friends and companions.

The invention has been described above with reference to one or more preferred embodiments. However, those skilled in the art will recognize that changes and modifications may be made in the described embodiments without departing from the nature and scope of the invention. For instance, the specific type and/or quantity of chemically reactive substance may vary in accordance with the situation or circumstances.

Various changes and modifications to one or more of the embodiments herein chosen for purposes of illustration will readily occur to those skilled in the art. To the extent that such modifications and variations do not depart from the spirit of the invention, they are intended to be included within the scope thereof, which is assessed only by a fair interpretation of the following claims.

Having fully described the invention in such clear and concise terms as to enable those skilled in the art to understand and practice the same, the invention claimed is:

1. A method of utilizing personal illicit drug detecting apparatus comprising the steps of:
   providing a substance chemically reactive to a suspected drug, the substance being provided in the form of a blend including the substance and finger nail polish;
   coating the substance and finger nail polish blend in the form of a layer on at least one finger nail of a user;
   moistening the layer on the at least one finger nail with liquid from a beverage possibly including the suspected drug; and
   observing any change of the layer, wherein the change indicates the presence of the suspected drug in the beverage.

2. A method of utilizing personal illicit drug detecting apparatus as claimed in claim 1 wherein the step of providing includes providing a plurality of substances chemically reactive to a plurality of suspected drugs, each of the plurality of substances being provided in the form of a separate blend including one each of the plurality of substances and finger nail polish.

3. A method of utilizing personal illicit drug detecting apparatus as claimed in claim 2 wherein the step of coating includes coating one each of the separate blends on different fingers nails.

4. A method of utilizing personal illicit drug detecting apparatus comprising the steps of:
  providing a substance chemically reactive to a suspected drug;
  coating the substance in the form of a layer on at least one finger nail of a user;
  moistening the substance on the finger nail with liquid from a beverage possibly including the suspected drug; and
  observing any change of the layer on the finger nail, wherein the change indicates the presence of the suspected drug in the beverage.

5. A method of utilizing personal illicit drug detecting apparatus as claimed in claim 4 wherein the step of providing includes blending the substance with finger nail polish and the step of coating includes painting the polish on the at least one finger nail.

6. A method of utilizing personal illicit drug detecting apparatus as claimed in claim 4 wherein the step of coating includes coating the substance in the form of a layer on each of a plurality of fingers nails and the step of moistening includes moistening the substance on each of the plurality of fingers nails at different times from the same or different beverages.

7. A method of utilizing personal illicit drug detecting apparatus as claimed in claim 4 wherein the step of providing includes providing a plurality of substances chemically reactive to a plurality of suspected drugs and the step of coating includes coating the plurality of substances, one each, on a similar plurality of finger nails.

8. A method of utilizing personal illicit drug detecting apparatus comprising the steps of:
  providing a substance chemically reactive to a suspected drug, the substance being provided in the form of a decal having a layer of the substance thereon; and
  positioning the decal on a finger of a user in one of the following positions: a finger nail, under a finger nail, and on the pad of a finger;
  moistening the decal with liquid from a beverage possibly including the suspected drug; and
  observing any change of the decal, wherein the change indicates the presence of the suspected drug in the beverage.

* * * * *